United States Patent [19]

Gulyás et al.

[11] Patent Number: 4,647,552

[45] Date of Patent: Mar. 3, 1987

[54] PROCESS FOR OBTAINING READY FOR FERTILIZATION SEXUAL PRODUCTS FROM SEXUALLY MATURE FISH

[75] Inventors: Tamás Gulyás, Szekszárd; Anikó Horváth, Budapest; György Kéri, Budapest; Károly Nikolics, Budapest; Balázs Szöke, Budapest; István Teplán, Budapest, all of Hungary

[73] Assignee: Kozponti Valto-es Hitelbank Rt. Innovacios Alap, Budapest, Hungary

[21] Appl. No.: 684,066

[22] Filed: Dec. 20, 1984

[30] Foreign Application Priority Data

Dec. 23, 1983 [HU] Hungary .................. 22514457/83

[51] Int. Cl.⁴ ............................................ A61K 37/24
[52] U.S. Cl. ...................................... 514/15; 514/800
[58] Field of Search ............................. 514/800, 15

[56] References Cited

U.S. PATENT DOCUMENTS

| | | | |
|---|---|---|---|
| 4,008,209 | 2/1977 | Fujino et al. | 514/800 |
| 4,083,967 | 4/1978 | Beddell et al. | 514/800 |
| 4,118,483 | 10/1978 | König et al. | 514/800 |
| 4,213,895 | 7/1980 | Immer et al. | 514/800 |
| 4,410,514 | 10/1983 | Vale, Jr. et al. | 514/800 |
| 4,530,920 | 7/1985 | Nestor et al. | 514/800 |

Primary Examiner—Delbert R. Phillips
Attorney, Agent, or Firm—Keil & Weinkauf

[57] ABSTRACT

The invention relates to a process for obtaining ready-for-fertilization sexual products from sexually mature fish in a period independent of their natural spawning season, in which actual stage of ripening is determined by probing of sexual products [sperm or eggs], fish not yet ripe for ovulation are separated from ripe fish, compounds of hormonal effect are administered to fish, and after the ovulation sexual products are obtained from the fish or from their environment.

In the process according to the invention a nonapeptide-$C_{1-4}$-alkyl-amide or a decapeptide amide of the general formula (I), $$\text{Glp-His-Trp-Ser-Tyr-}X_1\text{-}X_2\text{-}X_3\text{-Pro-}X_4 \quad (I)$$

wherein $X_1$ is a glycyl group or a D-isomer of any natural or synthetic amino acid group, $X_2$ represents an L-amino acid group having 1 to 4 carbon atoms in the side chain, L-phenyl-alanyl or L-tryptophyl group, $X_3$ represents an L-amino acid group having a $C_{1-4}$ alkyl or $C_{2-4}$ alkyl-amide side chain, $X_4$ is a glycine-amide or a $C_{1-4}$ alkyl-amide group, as well as salts or metal-complexes of these compounds are administered to fish in a dose of 0.1 μg to 5 mg, and to fish not yet ripe for ovulation the above quantities are administered in at least 2 but at most 12 portions, wherein the last dose used is at least the same or advantageously at least 1.5 times higher than the previous one.

The process according to the invention makes possible the obtaining of ripe sexual products ready for natural or artificial fertilization from any fish species in any period, independently of the natural spawning season of fish.

3 Claims, No Drawings

PROCESS FOR OBTAINING READY FOR FERTILIZATION SEXUAL PRODUCTS FROM SEXUALLY MATURE FISH

The invention relates to a process for obtaining ready-for-fertilization sexual products from sexually mature fish in a period independent of their natural spawning season.

It is known that the sexual activity in fish of both sexes is regulated by gonadotropic hormones released by the adenohypophysis. These hormones control the morphological and functional development and maturity of gonads, their gametogenetic activity (production of ova and spermatozoa) (gonads) and the excretion of gonadal hormones.

The adenohypophysis releases in both sexes the same two gonadotropic hormones. One of them is called FSH (follicle stimulating hormone), the other is known as LH (luteinizing hormone) or according to its effect in males ICSH (interstitial cell-stimulating hormone).

It is also known that these two hormones show no sex-specificity since the same FSH is responsible for the gametogenetic activity in males and females and the same LH or ICSH induces the excretion of androgen in males and of estrogen or progesterone in females.

Both the FSH and LH are glycoproteids which show a strong species-specificity in fishes.

The pituary of fish integrates the functions of the endocrine system and it has also some coordinating functions between the endocrine system and the nervous system, mainly through nuclei of the antonomic nervous system in the hypothalamus region of the diencephalon. Besides, the pituary regulates the reproduction cycle with the help of species-specific tropic hormones.

Under normal conditions ovulation of fish occurs in spawning environment characteristic of the given fish species. Ovulation of ripe eggs does not takes place spontaneously but the eggs remain in a dormant stage for a shorter or longer period till the development of appropriate conditions. This reproductive adaption characteristic for fish is jointly controlled by the hypophysis and the central nervous system. In dormant stage the organism of fish is balanced at a low level of gonadotropic activity, and thus only a very low amount of gonadotropin is released into the blood stream (Berbilsky N.: Sowremennoe nostoianie woprosa o nevrogormonalny reguliacii polowo cyclu ryb i bioteknika gormonalnyh wozdiestwii w rybowodstwe, Leningrad, 1966, Publisher: Gos. Univ., page 8).

It is impossible to determine the exact time when favourable conditions of fish appear since they develop in certain period more or less incidentally (e.g. late spring or early summer). It means that the regulating mechanism of reproduction in fish enables the adaption of reproductive cycle to the external environment. This regulation is co-ordinated in fish by the hypothalamus-hypophysis system.

According to the investigations carried out in the last few years it has been recognized that releasing of certain tropic hormones of the adenohypophysis is regulated by neurohormones. Neurohormones get out from terminal nerves running to certain nuclei of the hypothalamus and are absorbed at once by so-called portal capillary vessels, by this way they get through the blood directly to the sinuses of adenohypophysis.

All neurohormones known so far are oligopeptides or polypeptides. Neurohormones inducing the tropic hormone secretion are called "releasing factor" (RF), while those inhibiting the hormone secretion are called "inhibiting factor" (IF). According to the recent nomenclature, in case of neurohormones with known structure and function terms "releasing hormone" (RH) or "release inhibiting hormone" (RIH) are used.

It is characteristic of all neurohormones that their effect in hypophysectomized animals is analogous to the effect observed after administration of tropic hormones.

Basophiles of fish pituitary show seasonal changes, their quantity is decreasing in the spawning period. In the process of adaptation to the environment releasing hormones (RH) are produced which—through the blood-stream—get into the hypophysis and regulate there the releasing of tropic hormones to the blood. In this way fish are informed about coming into existence of the suitable external spawning conditions. As a consequence, the hypophysis and the excretion of gonadotrops into the blood are activated by the regulating hormone of luteinizing hormone (LH/RH) and the process of ovulation starts (Breton B. and Weil Cl., C.R. Acad. Sc., Paris, 277, 2061–2064 /1973/).

Sensory nerve impulses generated by the spawning ground are transmitted in this way to the endocrine system and this mechanism activates the reproductive system—having been in a compulsory dormant stage—in the moment when the optimal external environment is detected from the point of view of the survival of progeny (Gerbilsky, loc. cit.).

Neurohormones are interspecific in a high degree. Sequency of LH/RH in fish is different from that of the mammals, so they are not effective when interchanged.

Induced artificial propagation of fish has been made possible by finding and world-wide extension of the hypophysation technique (Gerbilsky, loc. cit.).

For hormonal inducing of ovulation pituitary glands collected from mature—or almost mature—common carps are mostly used after suitable preservation. Other natural or synthetic hormones tried so far gave no unanimously positive results.

As the common carp is widely cultured, there are large stocks all over the world from which pituitary glands can be easily collected in quantities sufficient for production purposes. Pituitary gland of common carp can be successfully used in the propagation of several cultured fish species. Taxonomically remote fish species (e.g. sturgeons) are exceptions, as in their case a hormonal suspension prepared from pituitary glands of the same species is used.

Collection and preservation of pituitary glands are carried out in the same way independently of the donor species. Pituitary glands should be collected from older—possibly sexually mature—fish. This is possible only very rarely. Pituitary gland is smaller in small fish; so—as it is dosed by weight—significantly more donor fish would be needed in case of small fish.

According to the known method pituitaries are dehydrated with aceton. After $3 \times 8$–12 hours of soaking in acetone pituitaries become free from water and fat. After hardening pituitary glands are dried for 24 hours at room temperature, meanwhile the acetone evaporates. Acetone is not injurious to the active gonadotropic ingredients of the pituitary and glands dried in the above way can be stored for a longer time without loss.

In order to activate gonadotropic hormones, glands are pulverized in a porcelain mortar and hormones are dissolved in fish-physiological saline solution (0.65 percent NaCl).

Hormone solution is injected into the muscles of fish so as to avoid flowing back or any other wastage. In case of small fish or fish with loose muscles, injections are administered into the body cavity. The injected pituitary hormones play the same role as the own hormones of the fish released at the detection of spawning environment: they generate the process of ovulation.

The hypophysation technique—although widely used in fish culture—is not effective in all cases. The main reasons of this are as follows:

(a) As the stage of ripening of donor fish—from which the pituitary glands were collected—is unknown, the gonadotropic hormone content of glands is also unknown. Therefore the effect is uncertain even if the doses were calculated with ample limits.

(b) Hormones of common carp pituitary are effective only in common carps and in species which are not remote taxonomically. Consequently several fish species—which are important from economical point of view—can be propagated only with low efficiency or cannot be propagated at all.

(c) With the aid of common carp (or any other) pituitary only LH effect has been achieved under commercial conditions, FSH effect cannot be produced by this way, probably because of reasons mentioned under (a).

(d) Owing to the lack of FSH effect hypophysation can be used only for induction of fish with eggs ripe for ovulation.

(e) In the case of hypophysation, induced artificial propagation can be carried out only in the natural spawning season; this means that the possibility is limited to a few days in a year. Thus, the utilization of production facilities is also limited.

(f) Collection of pituitary glands in large quantities can be carried out only from immature fish the pituitary of which is characterized by low gonadotropic activity. Collection from mature fish is possible only by killing valuable donor fish.

The invention aims at the elaboration of a process which makes possible the obtainment of ready for natural or artificial fertilization sexual products from any mature fish species.

The invention is based on the recognition that the above aim can be fully achieved if new gonadoliberin derivatives are administered into the organism of mature fish. We have found that FSH-LH/RH excreted in hypothalamus of fish can be succesfully substituted by these compounds, that is by injecting these compounds the development of sperm and eggs and the ovulation can be induced successfully.

Accordingly, the invention relates to a process for obtaining ready-for-fertilization sexual products from sexually mature fish in a period independent of their natural spawning season, in which actual stage of ripening of sexual products (sperm or eggs) of sexually mature fish is determined by probing, fish not yet ripe for ovulation are separated from ripe fish, compounds of hormonal effect are administered to fish, and after the ovulation sexual products are obtained from the fish or from their environment.

According to the invention, nonapeptide-$C_{1-4}$-alkyl-amides and decapeptide amides of the general formula (I), $$\text{Glp-His-Trp-Ser-Tyr-}X_1\text{-}X_2\text{-}X_3\text{-Pro-}X_4 \quad (I)$$

wherein
$X_1$ is a glycyl group or a D-isomer of any natural or synthetic amino acid group,
$X_2$ represents an L-amino acid group having 1 to 4 carbon atoms in the side chain, L-phenyl-alanyl or L-tryptophyl group,
$X_3$ represents an L-amino acid group having a $C_{1-4}$ alkyl or $C_{2-4}$ alkanoyl-amide side chain,
$X_4$ is a glycine-amide or a $C_{1-4}$ alkyl-amide group,
as well as salts or metal-complexes of these compounds—as compounds of hormonal effect—are administered to fish in a dose of 0.1 μg to 5 mg, advantageously 2 to 500 μg, preferably 5 to 100 μg, and in the case of fish not yet ripe for ovulation the above doses are administered in at least 2 but at most 12 portions wherein the last dose used is at least the same or preferably at least 1.5 times higher than the previous one.

The abbreviations in the formula are identical with the nomenclature accepted in peptide chemistry which is published e.g. in J. Biol. Chem. (241, 527/1966/; 247, 977/1972/).

The compound is non-toxic, so overdosage does not cause any harmful effect.

In case of treatment of fish not yet ripe for ovulation the number of injections depends on how far is the given fish from the stage of maturity for ovulation. If the desired stage is nearer, the number of injections will be lower.

Fish are ripe for ovulation if in the case of males the sperms become mobile when they come in contact with water and in the case of females the nucleus is situated on the periphery of the egg cell.

From among compounds of general formula (I) in the process according to the invention decapeptides of formula (II)

$$\text{Glp-His-Trp-Ser-Tyr-D-Phe-Leu-Gln-Pro-Gly-NH}_2 \quad (II)$$

and (III)

$$\text{Glp-His-Trp-Ser-Tyr-D-Phe-Trp-Leu-Pro-Gly-NH}_2 \quad (III)$$

can be used especially advantageously.

It is advisable to produce the compounds of general formula (I) used in the process according to the invention, by solid-phase technique of peptide synthesis (Merrifield R. B., J. Am. Chem. Soc., 85, 2149-2151/1963/). Depending on the structure of desired compounds, chloromethylated polystyrene-divinylbenzene resin is advantageously used in the case of peptide alkyl amide, and benzhydrylamine resin in the case of peptide amide. The amino acids are coupled to the resin as their N-α-tert-butyloxycarbonyl (Boc) derivatives, using dicyclohexylcarbodiimide (DCC), N,N'-diisopropylcarbodiimide (DIC) or active ester method. The end-product can be separated from the solid carrier by acidic or alkaline cleavage technique.

The required end-products of the general formula (I) can be built up from suitable protected amino acids by using an adequate combination of stepwise synthesis and fragment condensation, depending on the chemical character of the variable amino acid components.

Main advantages of the process according to the invention are as follows:

(a) It makes possible the propagation of fish species taxonomically remote from common carp which have not been propagated so far because of the lack of species-specific hypophysis.

(b) It can be used between ample ecological limits because the compounds of the general formula (I) exert their physiological effects even under very different biological conditions.

(c) The propagation of fish out of their natural spawning season and at the same time the full utilization of production facilities become possible.

(d) Absence of ovulation due to inaccurate dosage of hypophysis can be eliminated.

(e) The active ingredient used in the process of the invention can be produced synthetically in laboratories, whereby the uncertainty of effects characteristic of the known technique of hypophysation can be eliminated.

(f) The effect of the synthetic hormone used in the process is identical with that of the releasing of own gonadotropic hormones of fish.

(g) The synthetic hormone used in the process is interspecific, so it is efficient even in the case of taxonomically very different fishes.

The process according to the invention is further illustrated by the following examples, without limiting, however, the scope of protection.

EXAMPLE 1

Induced artificial propagation of sterlet (*Acipenser ruthenus* L.)

From the population of a given habitat mature fish are selected and then transported to the place of propagation. Sexes are segregated and the stage of ripening of eggs from females is determined. Fish are considered to be ripe for ovulation if the nucleus is situated on the periphery of the egg cell. Sperms of males are not examined as in the population of a given habitat the sexual products of males and females are practically in the same stage of ripening. If fish are ripe for ovulation, decapeptide of formula (II) in a single dose of 70 μg each is injected into each fish, including males.

If fish are not ripe for ovulation, they should be kept at the temperature of natural spawning and the above compound should be administered in doses of 10 μg each, at least 2 but at most 12 times as long as the nucleus moves from the centre to the periphery. The number of treatments depends on the actual stage of maturity of sexual products in comparison to the stage "ripe for ovulation". This process of ripening lasts at least 100 but at most 630 day-grades in the temperature interval of 12°–18° C. (Day-grade means number of days multiplied by the mean temperature of water used in the ripening period.)

Ovulation takes place 24–32 hours after the administration of the last dose. Thereafter sexual products are obtained in 40–60 minutes.

EXAMPLE 2

Induced artificial propagation of common carp (*Cyprinus carpio* L.)

In any season of the year and at any temperature mature breeders are selected from the stock and transported to the place of propagation. Sexes are segregated and the stage of ripening of sexual products is determined according to Example 1. If fish are ripe for ovulation, a single dose of 70 μg of decapeptide of formula (III) is administered, including males.

Fish not yet ripe for making ovulate should be kept at the temperature of natural spawning and the above-mentioned compound should be administered in doses of 5 μg each, at least 2 but at most 15 times as long as the nucleus of the egg cell moves from the centre to the periphery. The number of treatments depends on the actual stage of maturity of sexual products in comparison to the stage "ripe for ovulation". The process of ripening lasts at least 100 but most 750 day-grades in the temperature interval of 20°–24° C.

Ovulation takes place 240–260 hour-grades after the administration of the last dose. Then sexual products are stripped in 40–60 minutes.

EXAMPLE 3

Induced artificial propagation of perch [*Perca fluviatilis* L.]

Mature fish are selected from a population and transported to the place of propagation. Maturity of sexual products is determined according to Example 1 but sexes are not segregated. Fish ripe for ovulation—including males—are treated with a single dose of 20 μg of decapeptide of formula (II).

Fish not yet ripe for ovulation should be kept at the temperature of natural spawning and the above-mentioned compound should be administered in doses of 2 μg each at least 2 but at most 10 times as long as the nucleus of egg cell moves from the centre to the periphery. The number of treatments depends on the actual stage of maturity of sexual products in comparison to the stage "ripe for ovulation". The process of ripening lasts at least 100 day-grades, in extreme cases to 400 day-grades, in the water temperature-interval of 12°–16° C.

Spawning takes place 24–36 hours after the administration of the last dose. Perch can be spawned easily in tanks; in such a case stripping of sexual products is not necessary.

EXAMPLE 4

Induced artificial propagation of horse mackerel (*Trachurus trachurus* L.)

From among horse mackerels caught alive from the Adriatic in November specimens having a length of at least 240 mm are transported to the place of propagation. (Fish of this size are already mature sexually.) The compound of formula (II) is injected into each fish in a single dose of 10 μg. Ovulation takes place in 24 hours at the water temperature of 18°–24° C. Sexual products are obtained in 2 hours.

In case of horse mackerel the determination of stage of ripening and sex is unnecessary as ripe fish are at disposal in a practically unlimited quantity.

EXAMPLE 5

Induced artificial propagation of pike (*Esox lucius* L.)

Sexually mature fish are selected from a population and transported to the place of propagation. Sexes are segregated and the stage of ripening of sexual products is determined according to Example 1. Fish ripe for making ovulate—including males—are treated with a single dose of 100 μg of decapeptide of formula (II).

Fish not yet ripe for ovulation should be kept at the temperature of natural spawning and the above-given compound should be administered in doses of 5 μg each, at least 2 but at most 10 times as long as the nucleus of egg cell moves from the centre to the periphery. The number of treatments depends on the actual stage of maturity of sexual products in comparison to the stage "ripe for ovulation". The process of ripening lasts at least 70, in extreme cases to 350, day-grades at the water temperature of 8°–14° C.

EXAMPLE 6

Induced artificial propagation of silver carp (*Hypophthalmichthys molitrix* Val.)

Sexually mature fish are selected from the stock and transported to the place of propagation. Sexes are segregated. Stage of ripening of sexual products is determined according to Example 1 and fish ripe for ovulation—including males—are treated with a single dose of 100 μg of decapeptide of formula (III).

Fish not yet ripe for ovulation should be kept at the temperature of natural spawning and the above-mentioned compound should be administered in doses of 10 μg each, at least 2 but at most 10 times as long as the nucleus of egg cell moves from the centre to the periphery. The number of treatments depends on the actual stage of maturity of sexual products in comparison to the stage "ripe for ovulation". This process of ripening lasts at least 150, in extreme cases to 850, day-grades in the water temperature interval of 20°–26° C.

Ovulation takes place 240–260 hour-grades after the administration of the last dose. Thereafter sexual products are stripped.

We claim:

1. A process for obtaining ready-for-fertilization sexual products from sexually mature fish in a period independent of their natural spawning season, in which actual state of ripening is determined by probing of sexual products (sperm or eggs), fish not yet ripe for ovulation are separated from ripe fish, compounds of hormonal effect are administered to fish, and after ovulation sexual products are obtained from the fish or from their environment, characterized in that as compounds of hormonal effects nonapeptide-$C_{1-4}$-alkyl-amides and decapeptide amides of the general formula (I), $$\text{Glp-His-Trp-Ser-Tyr-}X_1\text{-}X_2\text{-}X_3\text{-Pro-}X_4 \qquad (I)$$

wherein
 $X_1$ is a glycyl, D-Phe, D-Ser, D-Trp or D-Ala group,
 $X_2$ is L-leucyl, L-phenylalanyl or L-tryptophyl group,
 $X_3$ is L-glutaminyl, L-asparaginyl or L-leucyl group,
 $X_4$ is glycylamide, or ethylamide, as well as salts or metal-complexes of these compounds are administered to fish in a dose of 0.1 μg to 5 mg, advantageously 2 to 500 μg, preferably 5 to 100 μg, and to fish not ripe yet for ovulation the above quantities are administered in at least 2 but at most 12 portions, wherein the last dose used is at least the same or advantageously at least 1.5 times higher than the previous one.

2. The process of claim 1 wherein the hormonal compound is Glp-His-Trp-Ser-Tyr-D-Phe-Leu-Gln-Pro-Gly-NH$_2$.

3. The process of claim 1 wherein the hormonal compound is Glp-His-Trp-Ser-Tyr-D-Phe-Trp-Leu-Pro-Gly-NH$_2$.

* * * * *